United States Patent [19]

Meakin

[11] 4,167,875
[45] Sep. 18, 1979

[54] FILTRATION METHOD AND APPARATUS

[76] Inventor: John C. Meakin, 23 The Gill, Pembury, Tunbridge Wells, Kent, England

[21] Appl. No.: 711,830

[22] Filed: Aug. 5, 1976

[51] Int. Cl.² ........................... G01N 1/14; G01N 1/34
[52] U.S. Cl. .................................. 73/421 R; 23/230.6; 23/920; 210/73 R; 210/205; 210/323 R; 210/387; 422/71; 422/101
[58] Field of Search ................. 23/259, 253 R, 230 R; 210/387, 400, 455, 409, 205, 323 R, 73 R; 73/421 R; 422/101

[56] References Cited

U.S. PATENT DOCUMENTS

| | | | |
|---|---|---|---|
| 3,138,015 | 6/1964 | Avery | 210/387 X |
| 3,269,800 | 8/1966 | Lukrec | 23/259 |
| 3,319,792 | 5/1967 | Leder et al. | 23/259 X |
| 3,554,700 | 1/1971 | Maxon | 23/253 R X |
| 3,684,452 | 8/1972 | Bessman | 23/259 X |
| 3,888,770 | 6/1975 | Avital et al. | 23/259 X |
| 3,923,463 | 12/1975 | Bagshawe et al. | 23/253 R |
| 3,923,463 | 12/1975 | Bagshawe et al. | 23/253 R |

FOREIGN PATENT DOCUMENTS 929079 6/1963 United Kingdom .................... 210/387

OTHER PUBLICATIONS

Treadwell et al., "Analytical Chemistry", vol. II, John Wiley & Sons; London; 1930; pp. 25-32.

Primary Examiner—Arnold Turk
Attorney, Agent, or Firm—A. W. Breiner

[57] ABSTRACT

Apparatus for treating samples comprising a sample holding element; a wash trough removably positioned over the sample holding element; transfer tubes or conduits in sample receiving contact with the sample holding element, extending through the wash trough to a transfer head positioned over a vacuum manifold which elements, in combination, deliver sample from the sample holding element directly to a plurality of filter discs in said vacuum manifold means. A cutter block is positioned between the transfer head and manifold. The apparatus is designed and arranged so that the cutter block will simultaneously cut and position a plurality of filter paper discs on said filter discs. A plurality of individual samples can be treated rapidly while minimizing the amount of filter paper used with assurance of quantitative sample transfer.

4 Claims, 4 Drawing Figures

FILTRATION METHOD AND APPARATUS

FIELD OF THE INVENTION

The present application is directed to an apparatus capable of rapidly filtering and/or treating a plurality of samples and, more particularly, to a microfilter and harvester particularly suitable for biochemical filtrations such as radioimmunoassay and lymphocyte harvesting.

BACKGROUND OF THE INVENTION

Various types of filtration apparatus have been in use for some time. Gooch or Buchner funnels which use circular filter elements made of glass or cellulosic fibers that are held flat against the perforations of the funnel are well known. Further, British Pat. No. 1,351,752 discloses a unitary disposable filtration apparatus which comprises a filter element, a molded plastic tubular holder having a flow passage therethrough, a molded plastic support holder in which the support member extends across the inside of the holder to support the filter element across the flow passage of the holder during filtration, and sealing means which interlock the support member to maintain pressure on the outer periphery of the filter element. A filter element is locked in position across the flow passage of the holder adjacent to the support member. Although the apparatus of the patent gives satisfactory results, it does not provide for rapid and simultaneous treatment of a plurality of samples.

Other apparatus are commercially known including those for use in biochemical filtration or sample testing applications, but such devices are relatively complex leading to relatively high costs and are cumbersome or inconvenient for use.

GENERAL DESCRIPTION OF THE INVENTION

The present invention comprises a filtration or sample treating device in which a plurality of samples can be filtered or treated simultaneously, or individually. The subject samples can be carried in a liquid vehicle as particular materials, or the samples can be liquid which are to be separated from an extraneous material or materials, or two or more liquids can be treated and/or separated, or the like, as will be apparent hereinafter.

The apparatus of the invention comprises a sample holding element, preferably a tray or microplate having a plurality of rows of wells for containing a plurality of samples, but can be individual holders such as test tubes. A wash trough is removably positioned over the sample holders. Tubes or conduits extend from the sample holders through the wash trough to a transfer head positioned directly above a vacuum manifold. The vacuum manifold on its top surface has a plurality of raised filter discs corresponding to the number of tubes or conduits, and guide pins directly behind the two outermost filter discs. The tubes or conduits from the transfer head are centered directly above the filter discs. Accordingly, when vacuum is applied to the vacuum manifold, sample is drawn from the sample holder through the tubes and transfer head and deposited on filter paper contained on the filter discs on the manifold. A cutter block element positioned between the transfer head and the filter manifold contains holes corresponding in number to the filter discs and the guide pins and, when in operable position rests on the vacuum manifold properly positioned by the guide pins and filter discs.

In operation of the device, the transfer head and cutter block are removed from the manifold, and a continuous sheet of glass fiber paper or similar paper, as will be more apparent hereinafter, is positioned over the row of raised filter discs on the vacuum manifold. The cutter block is placed over the paper and lowered over the guide pins onto the vacuum manifold. Gentle hand pressure forces the filter discs, which are slightly smaller in diameter than the holes in the filter block, away from the sheet, cutting a filter disc from the sheet for each filter disc. The paper discs are locked in position ready for use. The transfer head is placed over the cutter block and pressed lightly to create a vacuum-tight seal. Sample holders, such as a row of wells of a microplate, are suitably positioned and the transfer tubes and wash trough are brought in sample receiving contact with the sample holder. Vacuum is switched on to the vacuum manifold. The samples are transferred from the sample holders to the filter discs, and both the wells and discs are washed by filling or flushing wash solution through the wash trough. The vacuum is switched off, and the transfer head is removed. The cutter block is lifted clear and the discs which are retained in the cutter block can be transferred to suitable vials or test tubes for future work up. If the filtrate is also of value, individual collecting bottles or vials can be positioned below each of the filters to collect the filtrate; or the manifold can be compartmentalized to individually receive filtrate from each sample holder. Thereafter, the transfer head and cutter block are again removed from the manifold, the filter paper positioned so that the end holes fit over the paper guides on the manifold, and the cutter block again replaced to cut the discs; the operation continuing until all of the samples are treated.

A preferred embodiment of the invention is illustrated in the drawing in which-

Figure 1:
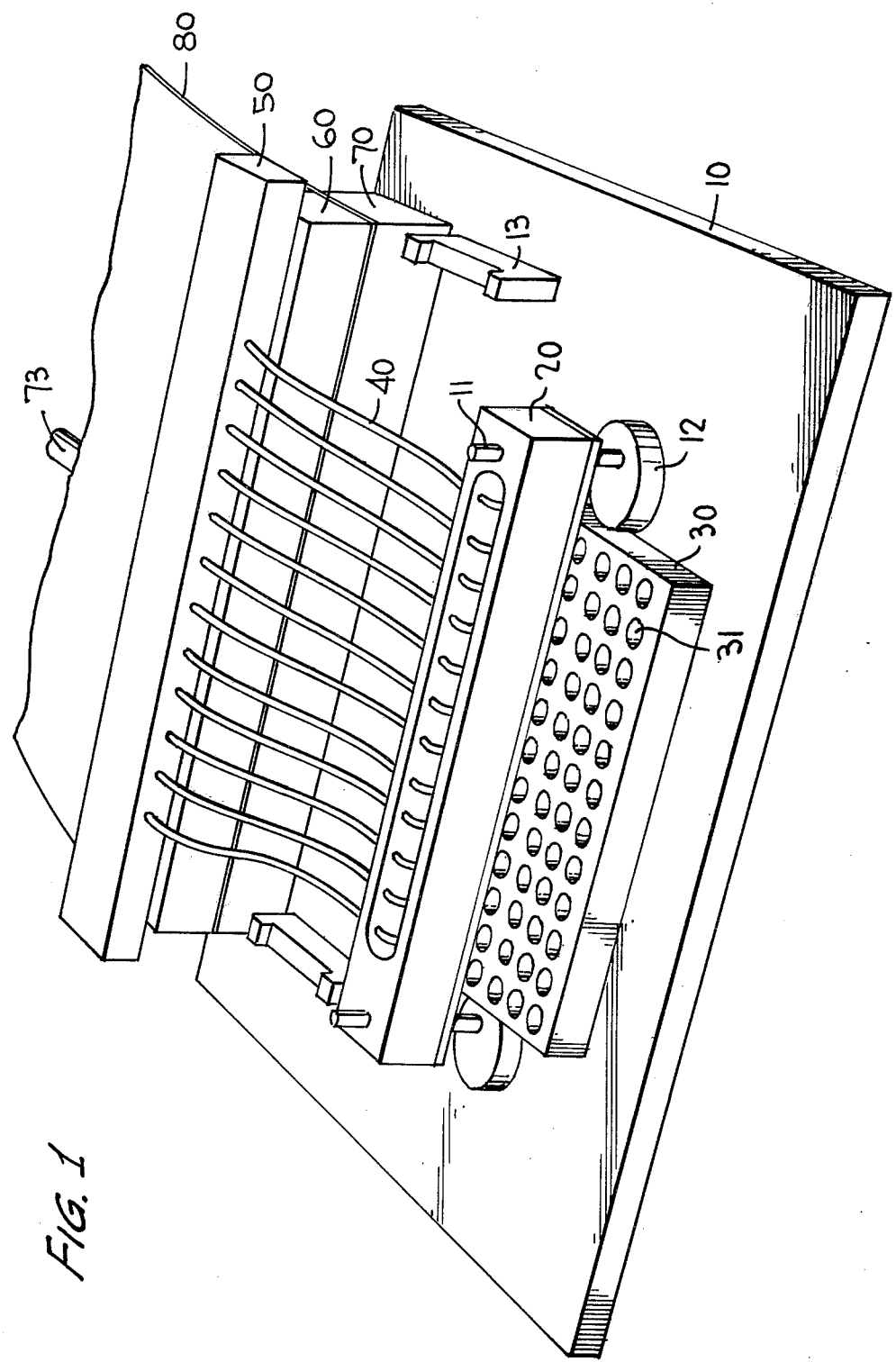
FIG. 1 is a front view of the apparatus.
Figure 2:
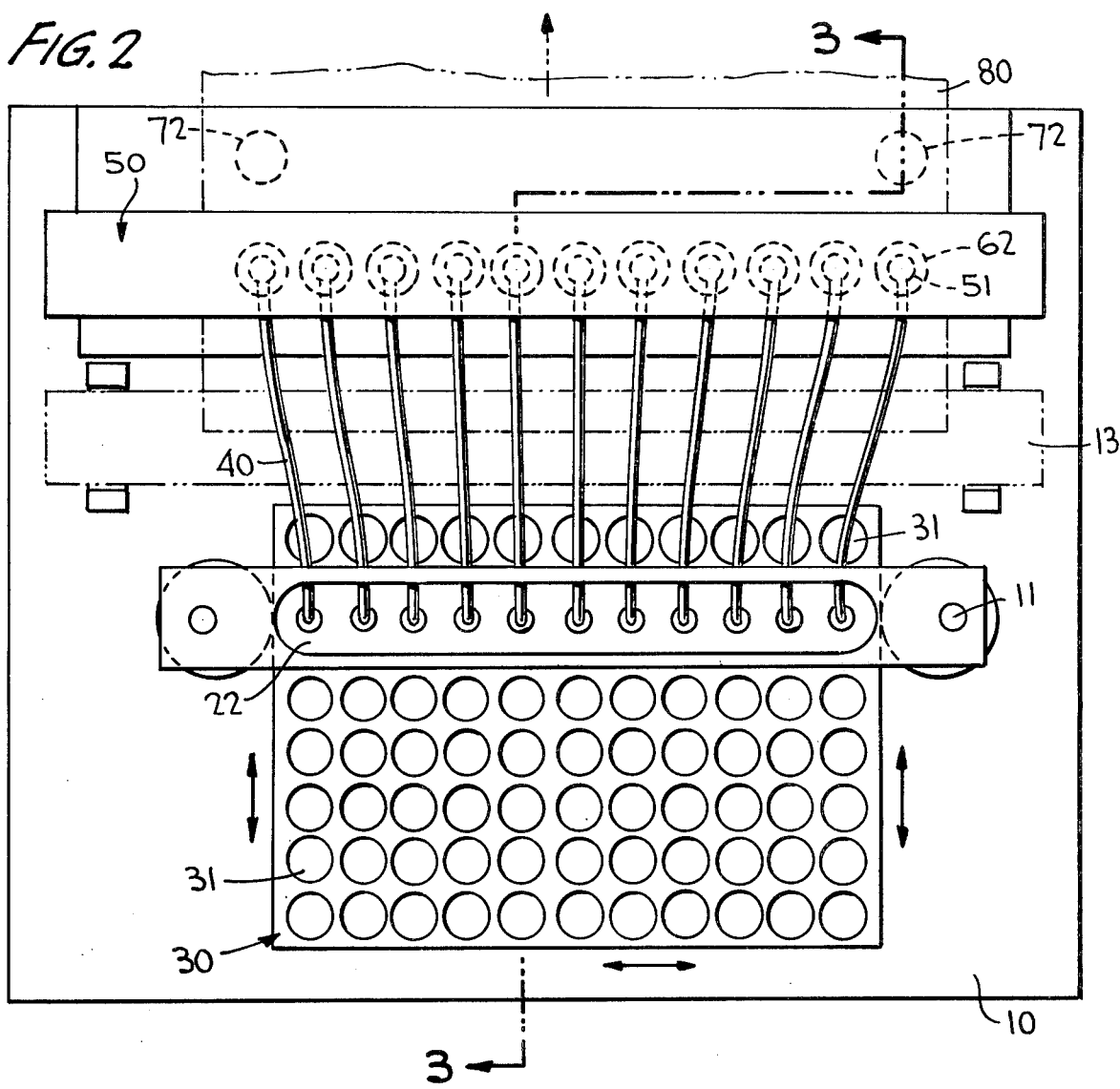
FIG. 2 is a top view of the apparatus of FIG. 1.
Figure 3:
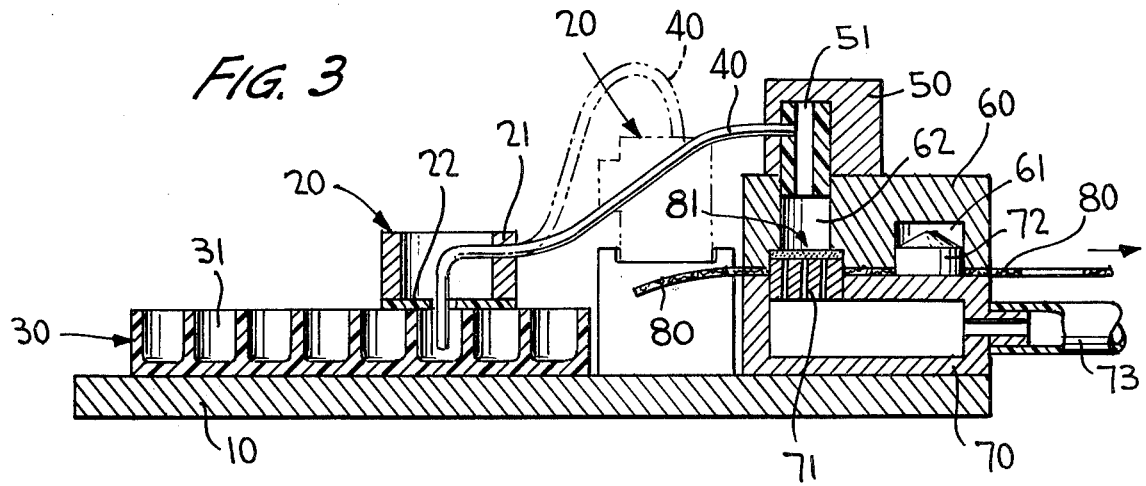
FIG. 3 is a cross-section along line 3—3 of FIG. 2.

Referring to the drawing, the apparatus comprises base 10. A wash trough 20 is removably positioned above a tray or microplate 30 on said base containing a series of wells 31. The wash trough is held in place above tray 30 by pins or spindles 11. The tray can be moved fore and aft by hand, and to and fro by turning eccentric wheels 12. As seen from FIG. 3, this wash trough can be removed from spindles 11 and held in holding bracket 13 when not in use. The samples to be treated are contained in wells 31. Tubes or conduits 40 are constructed and arranged with wash trough 20 so that they pass through the back wall 21 of the wash trough and then extend down through openings in the bottom wall 22 where they can be in sample receiving contact with wells 31 of tray 30. The openings in bottom wall 22 which are preferably a circular opening, as seen from FIGS. 2 and 3, are preferably larger than the conduits in order that the wash water or wash fluid passes to the outside of the tube or conduit, enhancing washing and transfer of sample. This arrangement permits simultaneously with sample transfer, and as a part thereof, flushing of the sample holder and sample with a wash solution to enhance the transfer of the sample to the sample treating and receiving elements. By suitably adjusting the degree to which the tube or conduit extends down into the well, the tube or conduit can be used as a means for scrapping the sides and/or bottom of the well to further enhance removal of sample, this being permitted by the fore and aft and to and fro movement of the tray as previously noted.

Figure 4:
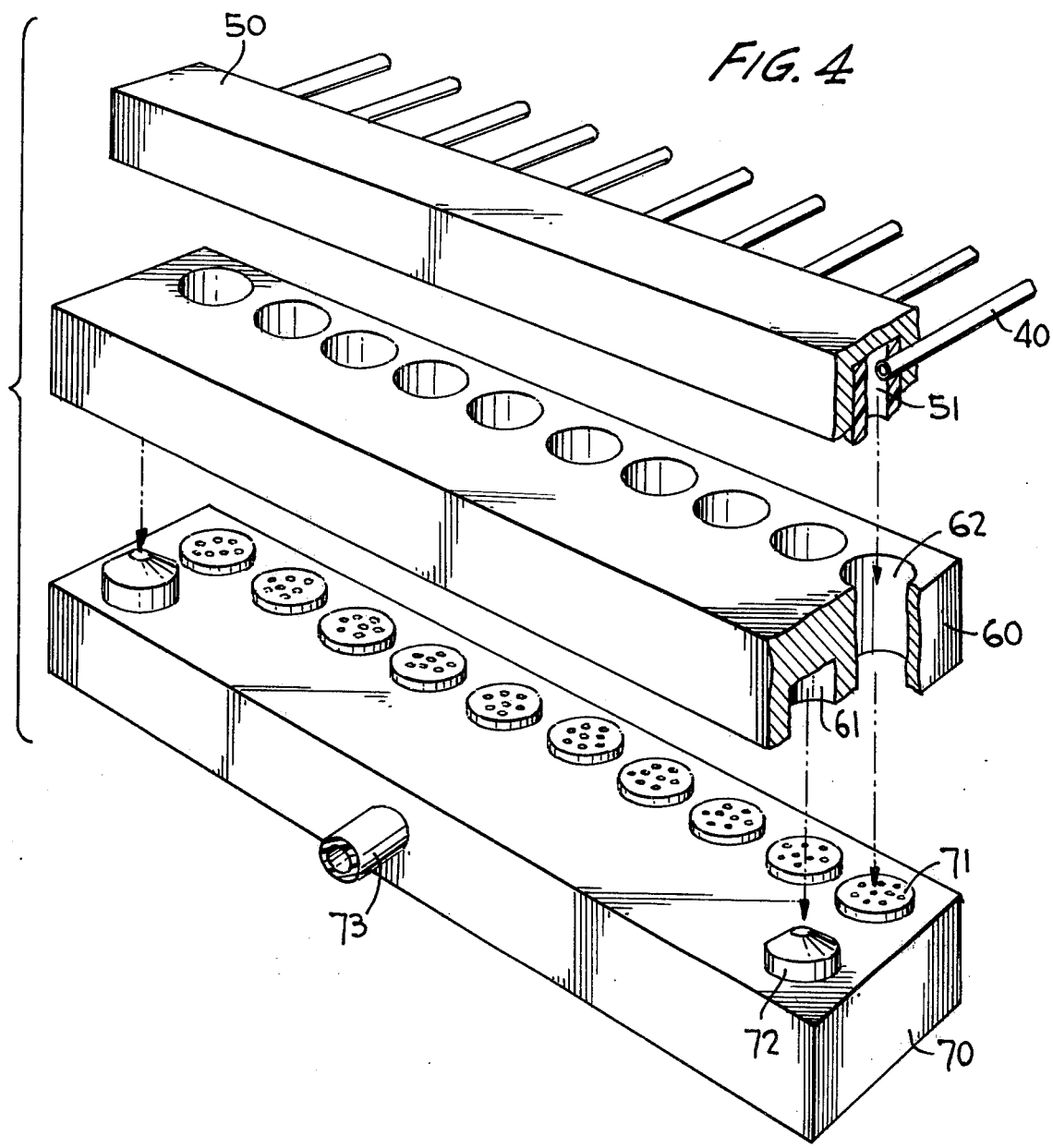
FIG. 4 is an exploded, partially broken-away view of the manifold, cutter block, and transfer head of the apparatus.

The conduits 40 extend from the back of the wash trough 20 to the front of transfer head 50 where they engage micro-bore tubes 51 within the transfer head which, as seen most clearly from FIGS. 3 and 4, are positioned directly above and extend into holes 62 of cutter block 60. Cutter block 60, in turn, is aligned with filter discs 71 through the opposite end of holes 62 and guide pins 72 in vacuum manifold 70.

Referring primarily to FIG. 4, vacuum manifold 70 has a plurality of discs 71 raised from the top surface thereof which extend down into manifold 70. There are also included directly behind the two outermost filter discs 71, guide pins 72 which are aligned with these filter discs. A vacuum line 73 to be connected to a suitable vacuum source, not shown, extends from the rear of the manifold. Cutter block 60 contains openings 61 extending partially into the block which line up with guide pins 72. A plurality of holes 62 correspond to and in cooperation with guide pins 72 line up the cutter block with filter discs 71 on manifold 70. As is apparent, the diameter of holes 61 and 62 are slightly larger than filter discs 71 and guide pins 72. Transfer head 50 sits on top of cutter block 60 and through the extension of micro-bore tubes 51 is held in place on top of cutter block 60 with each micro-bore being aligned with one hole 62. Gasket means, not shown, can be utilized between cutter block 60 and transfer head 50 and/or manifold 70 to maintain a vacuum seal if necessary. Preferably the parts will be machined to provide a vacuum seal without gasketing. Similarly, a gasket, not shown, can be provided between wash trough 20 and tray 30 to provide a vacuum seal.

Referring now to FIG. 3, in operation of the device a continuous sheet of filter paper, for example a sheet of glass filter paper 6.3 cm×18 cm, is positioned over the raised filter discs and the cutter block is gently, but firmly brought down onto filter paper 80. As seen from FIG. 3, as a result of raised filter discs 71, the cutting edge of the cutter block 60 shears the paper and positions a disc 81 directly on top of the filter. After sample is drawn from wells 31 of tray 30 and collected onto the filter disc 81, the cutter block is removed with the paper disc 81 being retained within the block. This permits ready transfer of the disc from the block into a suitable vial or test tube for further working up of the sample. Thereafter, the filter paper containing the first set of holes is moved rearward with respect to the filter disc of manifold 70 so that the outermost holes of the paper are positioned over guide pins 72. This assures alignment of the paper for the next cutting of paper discs and results in minimal loss of filter paper. The procedure is continued until the paper is completely used.

Although it is preferred, in accordance with the present invention, to cut the filter paper discs and transfer the discs from the cutter block after use individually, it is possible to work with a continuous sheet of paper whereby discs, through the cooperation of cutter block 60 and filter discs 71 of manifold 70, merely make an indentation or impression in the filter paper, permitting the collection of samples on spots of the entire sheet of paper. Thereafter the sheet is dried intact and only then are the individual circles torn out of the paper and collected for further work up. Complete or incomplete cutting through of the paper to obtain the indentation can be accomplished by lowering the height of filter discs 71, and/or enlarging hole 62. This latter method can also be desirable where the solid or the material retained on the filter paper is not of value and the wanted sample is retained in the filtrate and collected in a vial positioned below each of the filter discs.

The apparatus of the present invention has many applications due to its simplicity, compactness, and ability to treat a plurality of samples simultaneously. Obviously, however, in select instances it is possible to treat a relatively few samples or even treat an individual sample using the apparatus of the present invention. Moreover, the nature of the wash trough as shown and above described assures the substantial quantitative transfer of the sample from the plurality of wells of the tray to the filter paper. The apparatus is eminently useful, as previously noted, for radioimmunoassay and lymphocyte harvesting. However, as will be apparent, the apparatus can also be used in other typical biochemical investigations, for example, where radioactive labeled macro-molecular substance such as a protein is precipitated and washed. In this system aliquot portions of a reaction mixture are moved onto the disc in sequence. After the precipitation stage, low molecular weight compounds are washed from the disc by both aqueous acid solutions and water. The apparatus is allowed to dry, the upper portions removed, and the disc transferred to vials ready for measurement of their reactive content by scintillation counting. The apparatus of the present invention reduces the number of handling operations and, thus, is time saving. It also lowers the risk of damage to the adsorbent material which often results in low accuracy due to loss of radioactive material.

The apparatus may also be used in an analytical process in which a compound under examination may be trapped in a liquid treating element which is removed from the apparatus, the compound subsequently identified, and the amount present determined. This technique may be used, for example, in the routine assay of enzymes. The enzyme is incubated with a labeled substrate and the reaction terminated before transferring the mixture to the liquid treating element or elements in the apparatus. The free, non-ionic substances are then washed from the bound ionic material using either water or a dilute salt solution and the residue estimated by a radiometric procedure.

In accordance with the invention the filter paper can have various properties depending upon the ultimate application. For example, the paper can be hydrophobic which permits the separation of aqueous and water-immiscible phases. In this application oil and water may be separated. The use of hydrophobic paper would also allow the mixing of test samples of aqueous reagents such that both of the reagents remain in the body of the apparatus until the reaction is complete. Once the reaction is complete, the paper may be rendered non-hydrophobic by application of a polar solvent, or vacuum may be applied so that the reagent would pass through the paper.

For other applications, the paper may be chemically modified or treated in a manner such that undesirable or secondary reactions or interference with the liquid as it passes through the element is prevented. For example, a filter paper may be treated with a silicone compound to prevent protein adsorption.

In other embodiments, the liquid treating element may be an ion-exchange paper so that the apparatus becomes in effect an ion-exchange column. Various other modifications will be apparent to one skilled in the art. These modifications being known to those skilled in the art are covered in accordance with the present invention.

It is claimed:

1. An apparatus for treating a plurality of samples comprising, in combination, a base; a first plurality of individual sample-containing members positioned on said base; a wash trough adapted to hold wash material, said wash trough being positionable to be in operable association with a second plurality of said sample-containing members and including means whereby a wash material from said wash trough will flow to said second plurality of individual sample-containing members, said second plurality comprising the individual sample-containing members of said first plurality with said second plurality being numerically less than or equal to the first plurality; a transfer head containing transfer tubes in sample-receiving communication with said second plurality of sample-containing members extending through said wash trough; sample collection units in communication with said transfer head, said sample collection units including a filter support containing a plurality of raised filter discs equal to said second plurality of sample-containing members and a vacuum manifold means below said filter discs for drawing a vacuum across said plurality of filter discs; a cutter block having a plurality, equal to said second plurality, of openings therein positioned between said transfer head and filter support, said cutter block and filter discs on said filter support being constructed and arranged to cut upon bringing said cutter block and filter support into operable association a plurality of filter material discs equal in number to said filter discs and openings in said cutter block for filtering a sample contained in each of said second plurality of sample-containing members when a vacuum is applied to said vacuum manifold.

2. The apparatus of claim 1 wherein said filter support includes indexing means for positioning a filter material for forming said filter material disc.

3. The apparatus of claim 1 wherein said base includes means for positioning said sample-containing members.

4. The method of collecting samples including a filter step comprising the steps of providing a plurality of sample holders each containing a sample to be collected; simultaneously cutting a plurality of individual filter materials equal in number to said plurality of sample holders by pressing a cutter element into contact with a filter support; simultaneously transferring said samples from said sample holders to said individual filter materials on said filter support by applying a vacuum to said filter support, and simultaneously with said transfer and as a part thereof flushing said sample holders and samples with a wash solution, thereby enhancing the transfer of said samples to said individual filter materials.

* * * * *